（12） United States Patent
Patel et al.

(10) Patent No.: US 8,633,320 B2
(45) Date of Patent: Jan. 21, 2014

(54) PROCESS FOR PREPARING BROMO-SUBSTITUTED QUINOLINES

(75) Inventors: Nitinchandra D. Patel, Danbury, CT (US); Chris H. Senanayake, Brookfield, CT (US); Wenjun Tang, Shanghai (CN); Xudong Wei, Ridgefield, CT (US); Nathan K. Yee, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/318,706

(22) PCT Filed: May 3, 2010

(86) PCT No.: PCT/US2010/033340
§ 371 (c)(1),
(2), (4) Date: Feb. 22, 2012

(87) PCT Pub. No.: WO2010/129451
PCT Pub. Date: Nov. 11, 2010

(65) Prior Publication Data
US 2012/0165534 A1    Jun. 28, 2012

Related U.S. Application Data

(60) Provisional application No. 61/175,604, filed on May 5, 2009.

(51) Int. Cl.
*C07D 215/20* (2006.01)
*C07F 5/02* (2006.01)

(52) U.S. Cl.
USPC ............ 546/167; 546/173; 546/179; 548/110

(58) Field of Classification Search
None
See application file for complete search history.

(56) References Cited

U.S. PATENT DOCUMENTS

| 7,514,557 | B2 | 4/2009 | Busacca et al. |
| 7,608,614 | B2 | 10/2009 | Busacca et al. |
| 2006/0205638 | A1 | 9/2006 | Busacca et al. |
| 2010/0093792 | A1 | 4/2010 | Berkenbusch et al. |

FOREIGN PATENT DOCUMENTS

| WO | 98/45265 A1 | 10/1998 |
| WO | 2006/058201 A2 | 6/2006 |
| WO | 2007/022241 A2 | 2/2007 |
| WO | 2008/051272 A2 | 5/2008 |
| WO | 2009/014730 A1 | 1/2009 |
| WO | WO 2009005676 A2 * | 1/2009 |
| WO | 2010/033444 A1 | 3/2010 |

OTHER PUBLICATIONS

International Search Report, Form PCT/ISA/210, and Written Opinion, Form PCT/ISA/237, for corresponding PCT/US2010/033340; date of mailing: Aug. 18, 2010.
Cziaky et al., Synthesis of 2H-Pyrano[2,3-b]quinolines. Part I, Journal of Heterocyclic Chemistry, 1994, pp. 701-705, vol. 31.

* cited by examiner

*Primary Examiner* — Janet L Andres
*Assistant Examiner* — Timothy R Rozof
(74) *Attorney, Agent, or Firm* — Michael P. Morris; Philip I. Datlow

(57) ABSTRACT

Disclosed are methods for the preparation of bromo-substituted quinolines of the formula (I) where R is aryl, heteroaryl, alkyl, alkenyl or alkynyl, which are useful as intermediates in the preparation of agents for the treatment of hepatitis C viral (HCV) infections: Formula (I).

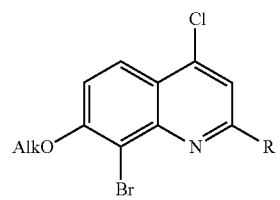

13 Claims, No Drawings

PROCESS FOR PREPARING BROMO-SUBSTITUTED QUINOLINES

BACKGROUND OF THE INVENTION

1. Technical Field

The application includes a description of improved processes for the preparation of bromo-substituted quinolines which are useful as intermediates in the preparation of agents for the treatment of hepatitis C viral (HCV) infections.

2. Background Information

The following schemes are known for preparing bromo-substituted quinolines.

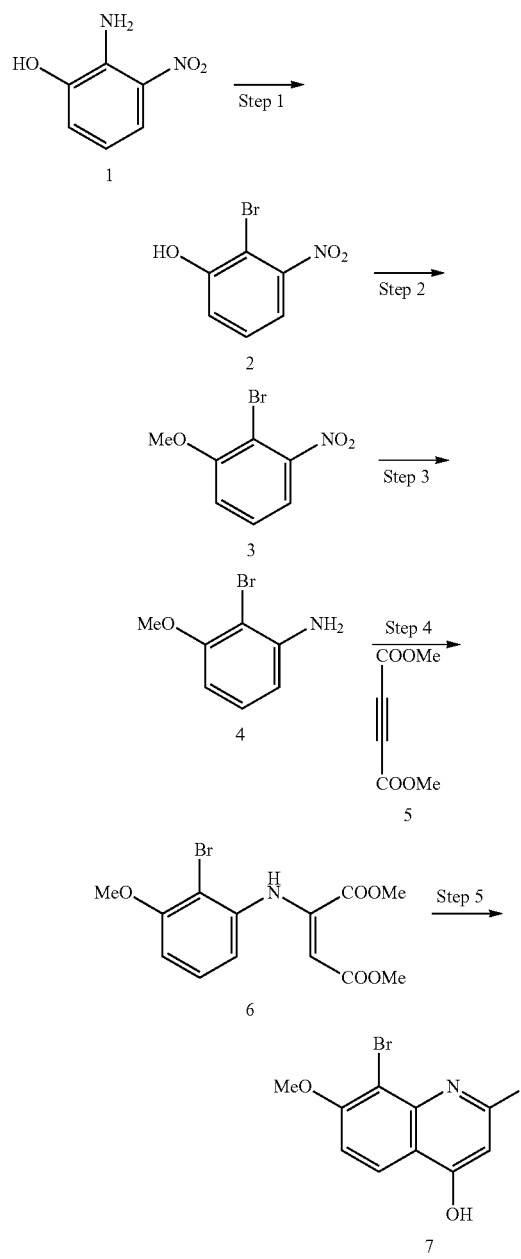

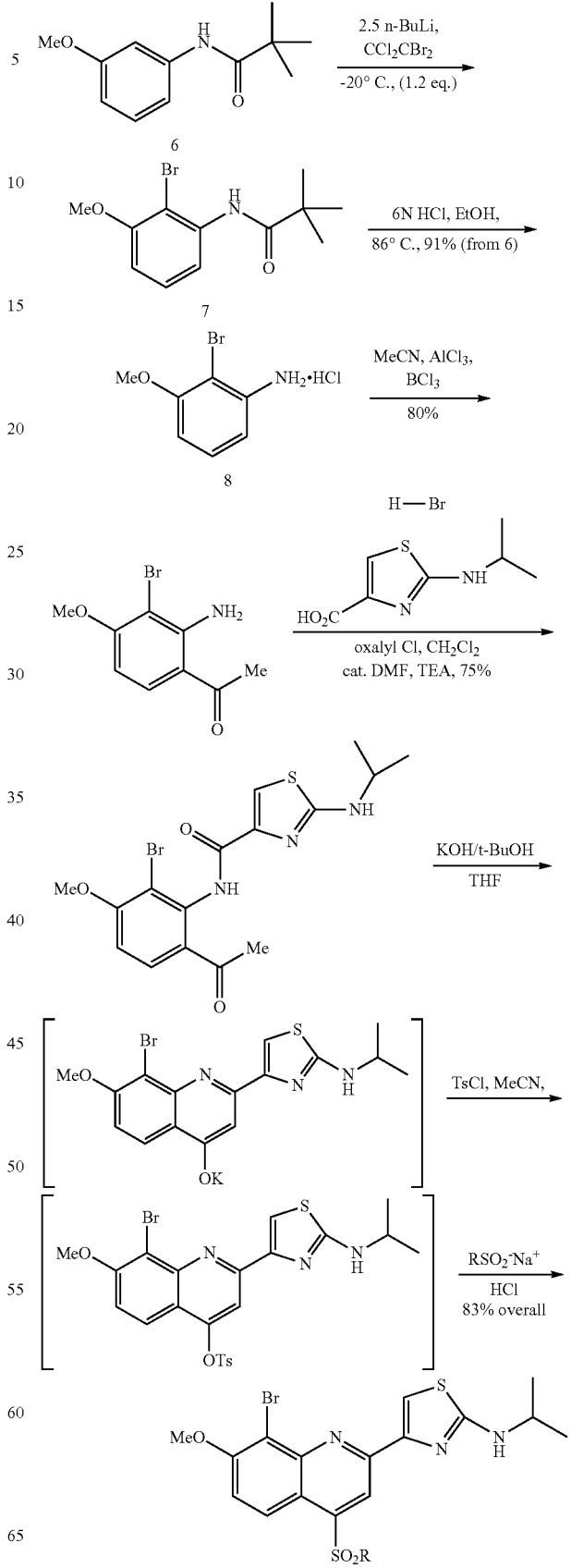

See, e.g., U.S. Pat. Nos. 7,514,557, 7,585,845 and 7,608,614. The prior schemes require a large number of steps to arrive at the bromo-substituted quinoline. The known syntheses of bromo-substituted quinolines in chemical development have been based on lithiation-bromination and Sugasawa reactions, which are not only lengthy but also require cryogenic conditions and/or intensive work-up procedures.

SUMMARY OF THE INVENTION

Among the problems addressed by the present invention is the provision of processes for preparing bromo-substituted quinolines that allows the use of economical reagents and requires a low number of steps. Bromo-substituted quinolines are useful intermediates in structure design of HCV protease inhibitors which are useful for the treatment of hepatitis C viral (HCV) infections. The invention includes a synthesis for these intermediates where rapid access to the bromo-substituted quinoline is achieved using a 2,4-dichloro-7-alkoxy quinoline. The 2,4-dichloro-7-alkoxy quinoline can be made by a known cyclization reaction from an m-alkoxy anilines, such as m-anisidine, with malonic acid (see, e.g., *Heterocyclic Communications*, vol. 7, no. 4, pp. 353-358 (2001)). The bromo-substituted quinoline is then made from the 2,4-dichloro-7-alkoxy quinoline directly by a bromination step. The resulting brominated quinoline can be subject to many types of Suzuki coupling reactions with boronic acids, boronate esters, potassium trifluoroborates or organoboranes to replace the chloro group at the 2-position with a variety of substituents. As a result, a range of substituted quinolines can be made efficiently in only 3 steps starting from the m-alkoxyaniline. Further, the bromination and Suzuki coupling steps can be conducted in a regioselective manner on these materials such that the position of the bromination and coupling is directed, for example, as shown below. This provides a much easier and flexible method for the synthesis of quinolines of the following formula (I) with a variety of substitution patterns.

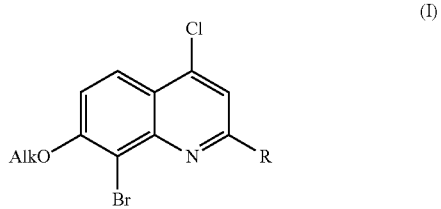

(I)

where R is: an aryl, alkyl, alkenyl or alkynyl group, the aryl groups preferably having 5-10 cyclic atoms which may be monocyclic or bicyclic, the alkyl groups preferably having 1-10 carbon atoms and the alkenyl or alkynyl groups preferably having 2-10 carbon atoms; and Alk is a lower alkyl group, for example $C_1$-$C_6$ alkyl. Preferably R is aryl, particularly: phenyl, naphthyl, furanyl, thiophenyl, indolyl, pyrazolyl, isoxazolyl or thiazolyl, each optionally substituted one or more times by halogen, alkyl, alkoxy, halogenated alkyl, —NH-alkyl or —NP-alkyl, where P is an amino protecting group such as tert-butyl ester (Boc). Preferably Alk is methyl.

The methods of the invention allow the use of inexpensive starting materials and reagents, and avoid the hazardous lithiation-bromination and Sugasawa steps employed in previous syntheses. In addition, this procedure minimizes the number of reagents and reactions for an overall faster cycle time.

DETAILED DESCRIPTION OF THE INVENTION

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined above and below, the number of carbon atoms is often specified preceding the group, for example, ($C_{1-10}$)alkyl means an alkyl group or radical having 1 to 10 carbon atoms and ($C_{3-7}$)cycloalkyl means a cycloalkyl group having from 3 to 7 carbon atoms in the ring. In general, for groups comprising two or more subgroups, the last named group is the point of attachment for the radical. For example, "cycloalkylalkyl" means a monovalent radical of the formula cycloalkyl-alkyl- and phenylalkyl means a monovalent radical of the formula phenyl-alkyl-. Unless otherwise specified below, conventional definitions of terms control and conventional stable atom valences are presumed and achieved in all formulas and groups.

The term "alkyl" as used herein, either alone or in combination with another substituent, means acyclic, straight or branched chain alkyl substituents. The term "lower alkyl" means an alkyl group with 1-6 carbon atoms. The term "alkenyl" as used herein, either alone or in combination with another substituent, means acyclic, straight or branched chain alkenyl substituents which contain at least one carbon-carbon double bond. The term "alkynyl" as used herein, either alone or in combination with another substituent, means acyclic, straight or branched chain alkenyl substituents which contain at least one carbon-carbon triple bond.

The term "alkoxy" as used herein, either alone or in combination with another substituent, means an alkyl group as defined above linked as a substituent through an oxygen atom: alkyl-O—.

The term "aryl" as used herein, either alone or in combination with another substituent, means either an aromatic cyclic system. For example, aryl includes a phenyl or a naphthyl ring system or an aromatic heterocyclic ring or ring system, see "heteroaryl" below.

The term "Het" as used herein, either alone or in combination with another substituent, means a monovalent substituent derived by removal of a hydrogen from a five-, six-, or seven-membered saturated or unsaturated (including aromatic) heterocycle containing carbon atoms and from one to four ring heteroatoms selected from nitrogen, oxygen and sulfur. Examples of suitable heterocycles for providing the Het groups include: tetrahydrofuran, thiophene, diazepine, isoxazole, piperidine, dioxane, morpholine, pyrimidine or

The term "Het" also includes those from a heterocycle as defined above fused to one or more other cyclic moiety, i.e., either a heterocycle or a carbocycle, each of which may be saturated or unsaturated. One such example includes thiazolo [4,5-b]-pyridine.

Although generally included within the term "Het", the term "heteroaryl" as used herein precisely defines an unsaturated heterocycle for which the double bonds form an aromatic system and is included within the term "aryl". Suitable examples of heteroaryl include: quinoline, indole, pyridine,

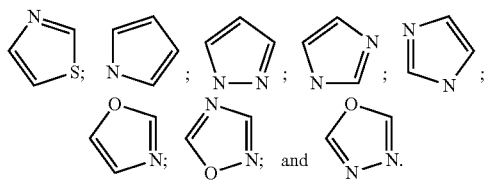

In general, all tautomeric forms and isomeric forms and mixtures, whether individual geometric isomers or optical isomers or racemic or non-racemic mixtures of isomers, of a chemical structure or compound are intended, unless the specific stereochemistry or isomeric form is specifically indicated in the compound name or structure.

The following chemicals may be referred to by these abbreviations:

| Abbreviation | Chemical Name |
|---|---|
| NBS | N-Bromosuccinamide |
| TFA | Trifluoroacetic acid |
| THF | Tetrahydofuran |
| $POCl_3$ | Phosphorus Oxide Trichloride (or Phosphorus Oxychloride) |
| EtOAc | Ethyl Acetate |
| DCM | Dichloromethane (or Methylene chloride) |
| iPrOH/IPA | Isopropyl Alcohol |
| NaOH | Sodium hydroxide |

In the synthetic schemes below, unless specified otherwise, all the substituent groups in the chemical formulas shall have the same meanings as described herein unless otherwise specified. The reactants used in the synthetic schemes described below may be obtained either as described herein, or if not described herein, are themselves either commercially available or may be prepared from commercially available materials by methods known in the art.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Examples section. Typically, reaction progress may be monitored by thin layer chromatography or High Pressure Liquid Chromatography (HPLC), if desired, and intermediates and products may be purified by chromatography on silica gel and/or by recrystallization, and characterized by one or more of the following techniques: NMR, mass spectroscopy and melting point.

In one embodiment, the present invention is directed to the following general multi-step synthetic method for preparing the compounds of formula I as set forth in Scheme I below. In other embodiments, the invention is directed to each of the individual steps of Scheme I and any combination of two or more successive steps of Scheme I. The invention may also be directed to the intermediate compounds set forth in Scheme I. Particularly, the bromination step alone and the Suzuki coupling reaction alone or together with other steps are separate embodiments of the invention. Also, the brominated compounds of formula (IV) resulting from the bromination reaction and certain Suzuki coupling reagent compounds of the formula (V) are separate embodiments of the invention.

An embodiment of the invention is shown by the following Scheme I including the initial cyclization reaction to the dichloroquinoline followed by regioselective bromination of dichloroquinoline and regioselective Suzuki coupling reactions:

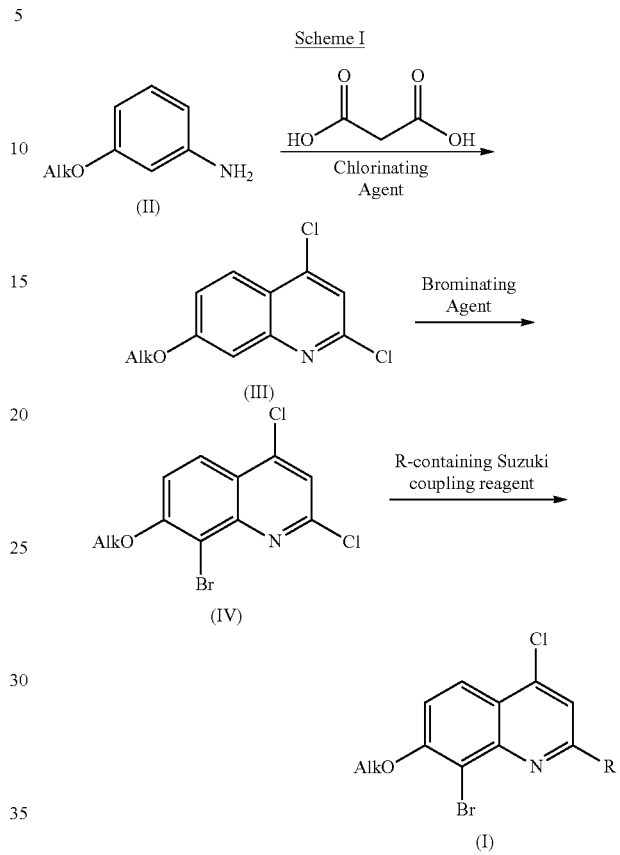

wherein R is: an aryl, heteroaryl, alkyl, alkenyl or alkynyl group, wherein the aryl or heteroaryl may each be optionally substituted with one or more groups independently selected from halogen, alkyl, halogenated alkyl, alkoxy, amido or amino optionally substituted by one or more alkyl and/or amino protecting groups; and Alk is a lower alkyl group.

The first step of the cyclization reaction of the m-alkoxy aniline with malonic acid is conducted in the presence of a chlorinating reagent. Any suitable chlorinating reagent can be used, for example: phosphorus oxide trichloride ($POCl_3$) phosphorus pentachloride, thionyl chloride, or triphenylphosphine dichloride. The cyclization reaction is preferably conducted with heating, for example, at 80-120° C. for 10-15 hours. Then, preferably, the product mixture is cooled, preferably below 30° C. Preferably, the resulting solid product is filtered and worked up, for example, with EtOAc and/or hexane rinsing.

The bromination reaction is conducted with a brominating reagent. Suitable brominating reagents include, for example, N-bromosuccinamide, bromine and 1,3-dibromo-5,5-dimethylhydantoin. The reaction may be conducted at about room temperature. The reaction is preferably conducted under acidic conditions, for example, by addition of an acid and preferably a strong acid, such as trifluoroacetic acid, sulfuric acid, benzensulfonic acid, or 10-camphorsulfonic acid. The reaction is also preferably conducted in the presence of an organic solvent which is immiscible in water to ease working up of the product. Suitable organic solvents include methylene chloride or 1,2-dichloroethane. For example, after reaction in the organic solvent, the reaction mixture can be quenched with a base, e.g., NaOH, and washed with water to separate an organic layer containing the product from an aqueous layer. The product is then worked up, for example, by distilling off the solvent, optionally adding a further solvent and distilling, and drying the product.

The Suzuki coupling reaction is preferably conducted in the presence of a base, for example potassium bicarbonate, to activate the coupling reagent and in the presence of a palladium catalyst, particularly a palladium catalyst with phosphine ligands, such as $Pd(PPh_3)_4$. The coupling reagent is an R-boronic acid, R-boronate ester, R-potassium trifluoroborate or R-organoborane. It is preferably an aryl boronic acid or ester which results in replacing the 2-chloro group with the aryl group. Particularly, the coupling reagent is a boronic acid of the formula R—B(OH)$_2$ or a boronate ester of the formula R—B(OR')$_2$ where R' is preferably Alk, or the coupling reagent is a boronate ester of the formula:

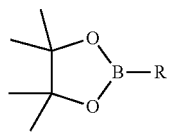

(V)

In one aspect, the coupling reagent is of the formula (V) where R is an optionally substituted thiazol-2-yl, e.g. substituted in the 5-position, by —NH-alkyl or —NP-alkyl, where P is an amino protecting group such as tert-butyl ester (Boc). The reaction is preferably conducted with heating to 50-100° C. and preferably under an inert atmosphere, e.g., nitrogen gas.

In another embodiment, the resulting compound (I) of the above embodiment is further reacted to replace the 4-chloro group with —SO$_2$Me, as shown in Scheme II below:

Scheme II

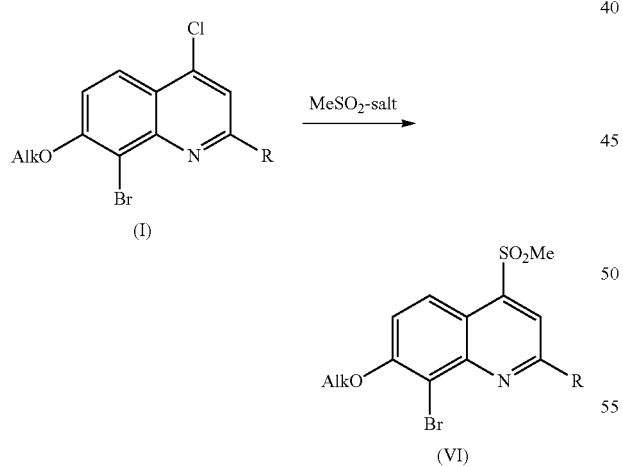

This reaction is conducted under acidic conditions with a MeSO$_2$ salt, for example, MeSO$_2$Na. Under analogous conditions compounds of the formula (VI) but having an arylsulfonyl or heteroaryl-sulfonyl group at the 4 position may be prepared. Such processes are described in U.S. Pat. Nos. 7,514,557 and 7,608,614.

Examples of the final compounds of formulas (I) and (VI), including compounds of formula (VI) having an aryl-sulfonyl or heteroaryl-sulfonyl group at the 4 position, which can be prepared by the distinct methods of the current invention are described in U.S. Pat. Nos. 7,514,557 and 7,608,614, all incorporated by reference herein. These publications also teach synthesis schemes by which the compounds prepared by this invention, i.e., of formulas (I) and (VI), can be used to prepare the final anti-HCV agents. Further examples of particular compounds of formula (VI) prepared by the process of the instant invention are as follows:

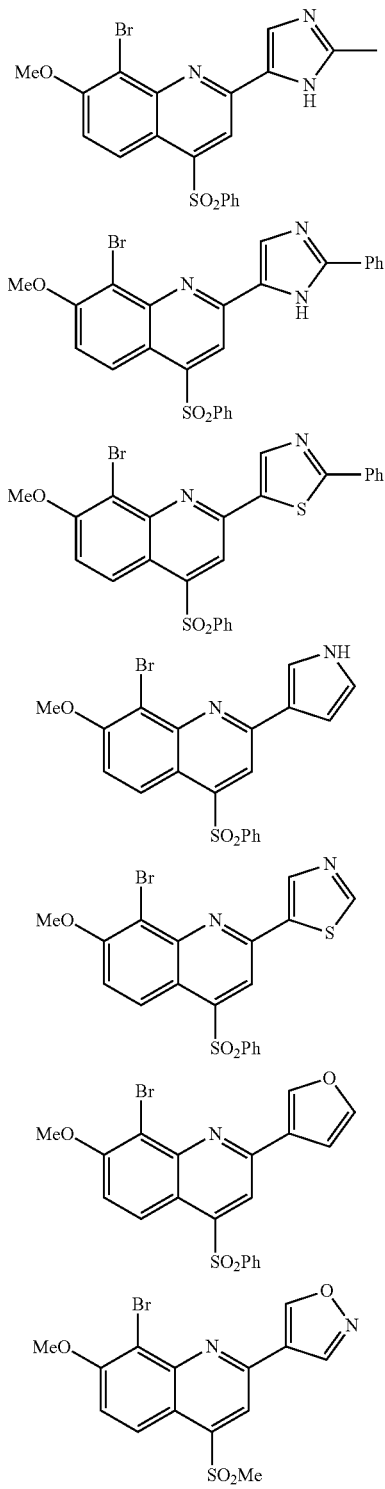

-continued

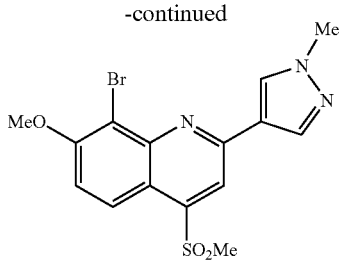

EXAMPLES

Step 1—Preparation of 2,4-dichloro-7-methoxy-quinoline

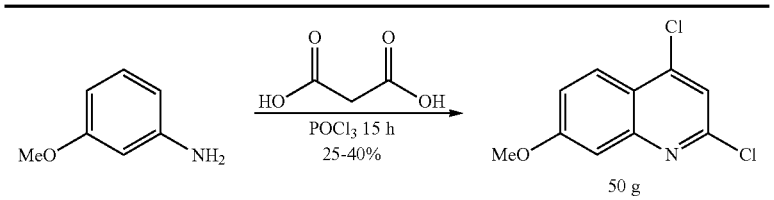

| Compound | Source | Content | Amount | MW | mmol | Equiv |
|---|---|---|---|---|---|---|
| m-Anisidine | Aldrich | 97% | 30.78 g | 123.15 | 250.00 | 1.0 |
| Malonic acid | Aldrich | 99% | 26.015 g | 104.06 | 250.00 | 1.0 |
| POCl$_3$ | Fluka | ≥98% | 312.55 g (190.00 mL) | 153.33 | 2038 | 8.15 |
| Ice | DI | | 500 g | 18.0 | | Solvent |
| Water | DI | | 1.7 Lt | 18.0 | | Solvent |
| EtOAc | EMD | ACS | ~600 mL | | | Solvent |
| Hexane | EMD | ACS | ~275 mL | | | Solvent |

1. Charged m-anisidine, malonic acid and POCl$_3$ into 500 mL jacketed reactor.
2. Stirred the mixture at reflux (100-105° C.) for 10-15 h.
3. Poured the mixture into ice-water (2.2 Lt) slowly while keeping the temperature below 30° C.
4. Filtered solid and rinsed with water and air dried for 2 h.

5. Dissolved solids in EtOAc (400 mL) at 50° C. and then filtered through a pad of silica gel and charcoal and rinsed with 1:1 mixture of EtOAc/hexane (300 mL).
6. Distilled EtOAc up to minimum volume of 200 mL then added hexane (100 mL) slowly and then stirred at room temperature for 2 h.
7. Filtered the solids, rinsed with EtOAc/hexane (1:1 mixture, 75 mL) and air dried for 2 h and then at 50° C. for 12 h to afford the product in the following batches. 1st crop: 11.4 g, 97.01% pure. 2nd crop: 2.7 g, 95.3% pure.

Step 2—Preparation of 8-bromo-2,4-dichloro-7-methoxy-quinoline

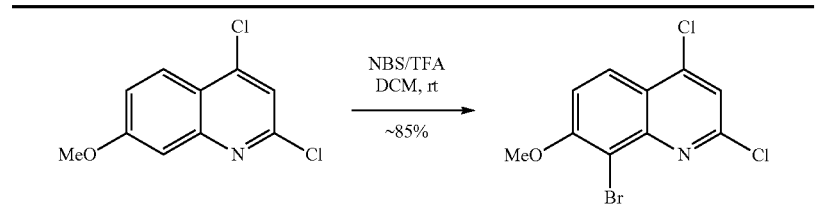

| Compound | Source | Content | Amount | MW | mmol | Equiv | density |
|---|---|---|---|---|---|---|---|
| 2,4-dichloro-7-methoxy quinoline | | >98.5% | 31.05 g | 228.07 | 136.14 | 1.0 | — |
| NBS | Aldrich | Reagent plus | 26.65 g | 177.98 | 150.00 | 1.10 | — |
| DCM | EMD | ACS | 620 mL | — | — | — | 1.325 |
| TFA | Aldrich | 99% | 38.80 g | 114.02 | 340.35 | 2.5 | — |
| iPrOH | EMD | ACS | 250 mL | | | | |
| 1M NaOH | EMD | 47022713 | 88 mL | 40.00 | 400.00 | 2.94 | — |
| iPrOH (rinse) | EMD | ACS | 25 mL | — | — | — | — |

1. Charged 2,4-dichloro-7-methoxy quinoline (31.05 g, 136 mmol) and methylene chloride (620 mL).
2. Cooled the mixture to 0° C. and charged TFA (2.5 eq) and NBS (1.15 eq) and then warmed the mixture to room temperature.
3. Stirred at room temperature for 2 h.
4. Quenched with 1M NaOH (~349 mL, 40 mmol) to adjust the pH to 7 and separated the layers.
5. Washed with water (403 mL) and allowed the layers to separate. Collected organic layer.
6. Distilled solvent using rotovap under reduced pressure and solvent switched to IPA (250 mL).
7. Heated to 70° C. and then cooled to 22° C. over 2 h and treated with 1M NaOH (88 mL, 0.5 eq) at room temperature and stirred for 30 min.
8. Filtered and rinsed with 1:3 mixture of IPA/Water (100 mL) and water (250 mL) and dried under vacuum at 50° C. to afford 37.62 g of product (90% yield) as beige/tan solid. HPLC area % purity: ~95.1%.

Step 3—Suzuki Coupling Reaction

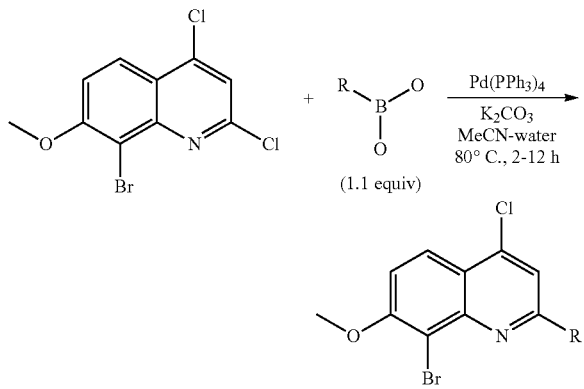

To a mixture of 8-bromo-2,4-dichloro-7-methoxy-quinoline (100 mg, 0.32 mmol), the boronic acid (1.1 equiv), $K_2CO_3$ (90 mg, 0.65 mmol, 2.0 equiv), and $Pd(PPh_3)_4$ (7.5 mg, 0.007 mmol, 0.02 equiv) was added degassed MeCN (3 mL) and water (1 mL). The mixture was stirred under $N_2$ at 80° C. for 2-12 h until the starting material was completely consumed, then quenched at room temperature by addition of EtOAc (5 mL) and water (5 mL). The EtOAc layer was washed with water (10 mL), brine (10 mL), dried over $Na_2SO_4$, concentrated, and purified by column chromatography (hexane: $CH_2Cl_2$) to give the desired product.

In a manner analogous to the above-described Example, the following compounds were prepared:

8-Bromo-4-chloro-7-methoxy-2-phenyl-quinoline

77%, $^1$HNMR (400 MHz, $CDCl_3$): δ=8.26 (d, J=9.9 Hz, 2H), 8.11 (d, J=9.2 Hz, 1H), 7.87 (s, 1H), 7.50 (m, 3H), 7.29 (d, J=9.2 Hz, 1H), 4.06 (s, 3H); $^{13}$CNMR (100 MHz, $CDCl_3$): δ=157.9, 157.8, 146.9, 143.1, 138.1, 130.1, 128.9, 127.6, 124.3, 121.2, 117.0, 113.9, 111.3, 56.9; ESI-MS: m/z 350 $[M+H]^+$.

8-Bromo-4-chloro-2-(4-fluoro-phenyl)-7-methoxy-quinoline

80%, $^1$HNMR (400 MHz, $CDCl_3$): δ=8.26 (t, J=8.0 Hz, 2H), 8.25 (d, J=8.8 Hz, 1H), 7.84 (s, 1H), 7.34 (d, J=9.6 Hz, 1H), 7.20 (t, J=8.4 Hz, 2H), 4.09 (s, 3H); $^{13}$CNMR (100 MHz, $CDCl_3$): δ=165.5, 163.0, 157.9, 156.7, 146.8, 143.2, 134.2 (d, J=3.0 Hz), 131.1 (d, J=9.0 Hz), 129.5 (d, J=9.0 Hz), 125.8, 124.3, 121.1, 116.6, 115.9, 115.7, 114.0, 56.9; ESI-MS: m/z 368 $[M+H]^+$.

8-Bromo-4-chloro-2-(4-ethoxy-phenyl)-7-methoxy-quinoline

58%, $^1$HNMR (400 MHz, $CDCl_3$): δ=8.23 (d, J=8.0 Hz, 2H), 8.13 (d, J=9.2 Hz, 1H), 7.84 (s, 1H), 7.29 (d, J=8.8 Hz), 7.01 (d, J=8.0 Hz), 4.12 (m, 2H), 4.08 (s, 3H), 1.45 (t, J=6.4 Hz, 3H); $^{13}$CNMR (100 MHz, $CDCl_3$): δ=160.9, 157.8, 157.6, 147.0, 142.9, 130.6, 129.1, 124.3, 120.9, 116.6, 114.8, 113.5, 111.2, 63.6, 57.0, 14.8; ESI-MS: m/z 394 $[M+H]^+$.

8-Bromo-4-chloro-7-methoxy-2-(4-trifluoromethyl-phenyl)-quinoline

60%, $^1$HNMR (400 MHz, $CDCl_3$): δ=8.36 (d, J=8.4 Hz, 2H), 8.18 (d, J=9.2 Hz, 1H), 7.89 (s, 1H), 7.76 (d, J=9.2 Hz, 1H), 7.37 (d, J=9.1 Hz, 1H), 4.10 (s, 3H); $^{13}$CNMR (100 MHz, $CDCl_3$): δ=158.1, 156.3, 147.0, 143.6, 141.4, 131.8 (q, J=32.3 Hz), 128.0, 125.8 (q, J=3.7 Hz), 124.4, 121.5, 117.0, 114.6, 111.5, 57.1; ESI-MS: m/z 417 $[M+H]^+$.

8-Bromo-4-chloro-7-methoxy-2-m-tolyl-quinoline

89%, $^1$HNMR (400 MHz, $CDCl_3$): 8.12 (d, J=9.2 Hz, 1H), 8.08 (s, 1H), 8.04 (d, J=7.6 Hz, 1H), 7.87 (s, 1H), 7.40 (t, J=7.6 Hz, 1H), 7.29 (m, 1H), 5.28 (s, 1H), 4.06 (s, 3H), 2.47 (s, 3H); $^{13}$CNMR (100 MHz, $CDCl_3$): δ=158.1, 157.8, 147.0, 143.0, 138.6, 138.1, 131.0, 128.8, 128.3, 124.8, 124.3, 121.2, 117.2, 113.9, 111.3, 57.0, 21.6; ESI-MS: m/z 364 $[M+H]^+$.

8-Bromo-4-chloro-7-methoxy-2-(2-methoxy-phenyl)-quinoline

64%, $^1$HNMR (400 MHz, $CDCl_3$): δ=8.19 (dd, J=7.6, 1.6 Hz, 1H), 8.16 (d, J=9.2 Hz, 1H), 8.11 (s, 1H), 7.42 (m, 1H), 7.33 (d, J=9.2 Hz, 1H), 7.14 (dt, J=7.6, 1.2 Hz, 1H), 7.01 (d, J=8.4 Hz, 1H), 4.07 (s, 3H), 3.91 (s, 3H); $^{13}$CNMR (100 MHz, $CDCl_3$): δ=157.7, 157.6, 157.5, 146.9, 141.5, 132.3, 131.2, 128.1, 124.3, 121.9, 121.5, 121.1, 113.9, 111.6, 111.3, 57.0, 55.7; ESI-MS: m/z 380 $[M+H]^+$.

8-Bromo-4-chloro-7-methoxy-2-naphthalen-2-yl-quinoline

86%, $^1$HNMR (400 MHz, $CDCl_3$): δ=8.68 (s, 1H), 8.51 (d, J=6.8 Hz, 1H), 8.18 (d, J=9.2 Hz, 1H), 8.06 (s, 1H), 8.99 (m, 2H), 7.89 (m, 1H), 7.54 (m, 2H), 7.35 (d, J=9.2 Hz, 1H), 4.10 (s, 3H); $^{13}$CNMR (100 MHz, $CDCl_3$): δ=135.5, 134.3, 133.4, 129.0, 128.7, 127.8, 127.5, 127.1, 126.4, 124.9, 124.4, 121.3, 117.3, 114.0, 111.4, 57.0; ESI-MS: m/z 400 $[M+H]^+$.

8-Bromo-4-chloro-2-furan-3-yl-7-methoxy-quinoline

94%, $^1$HNMR (400 MHz, $CDCl_3$): δ=8.20 (s, 1H), 8.15 (d, J=9.2 Hz, 1H), 7.59 (s, 1H), 7.54 (s, 1H), 7.33 (d, J=9.2 Hz), 7.14 (s, 1H), 6.09 (s, 3H); $^{13}$CNMR (100 MHz, $CDCl_3$): δ=157.9, 152.8, 147.1, 144.2, 142.9, 134.4, 127.3, 124.4, 121.1, 117.2, 113.6, 110.9, 109.1, 57.0; ESI-MS: m/z 340 $[M+H]^+$.

8-Bromo-4-chloro-7-methoxy-2-thiophen-3-yl-quinoline

88%, $^1$HNMR (400 MHz, $CDCl_3$): δ=8.15 (d, J=9.6 Hz, 1H), 8.13 (m, 1H), 7.93 (dd, J=5.2, 1.2 Hz, 1H), 7.77 (s, 1H), 7.44 (dd, J=4.8, 2.8 Hz, 1H), 7.33 (d, J=9.2 Hz, 1H), 4.09 (s, 3H); $^{13}$CNMR (100 MHz, CDCl$_3$): δ=157.9, 154.1, 147.1, 143.0, 141.6, 126.9, 126.6, 125.9, 124.4, 121.2, 117.3, 113.8, 111.1, 57.0; ESI-MS: m/z 356 [M+H]$^+$

8-Bromo-4-chloro-2-(1H-indol-5-yl)-7-methoxy-quinoline

84%, $^1$HNMR (400 MHz, DMSO-D6): δ=8.63 (d, J=1.2 Hz, 1H), 8.34 (s, 1H), 8.24 (dd, J=8.8, 2.0 Hz, 1H), 8.18 (d, J=9.2 Hz, 1H), 7.64 (d, J=9.2 Hz, 1H), 7.56 (d, J=8.4 Hz, 1H), 7.44 (d, J=1.2 Hz, 1H), 6.60 (d, J=2.8 Hz), 4.07 (s, 3H); $^{13}$CNMR (100 MHz, DMSO-D6): δ=156.9, 155.9, 144.3, 140.2, 135.6, 126.6, 126.2, 124.9, 122.4, 119.1, 118.4, 118.2, 115.0, 112.7, 110.0, 107.9, 100.6, 55.2; ESI-MS: m/z 389 [M+H]$^+$.

8-Bromo-4-chloro-7-methoxy-2-(1-methyl-1H-pyrazol-4-yl)-quinoline

82%, $^1$HNMR (400 MHz, CDCl$_3$): δ=8.18 (s, 1H), 8.13 (d, J=9.2 Hz, 1H), 8.07 (s, 1H), 7.58 (s, 1H), 7.29 (d, J=9.2 Hz, 1H), 4.08 (s, 3H), 4.00 (s, 3H); $^{13}$CNMR (100 MHz, CDCl$_3$): δ=157.9, 153.1, 147.2, 142.8, 138.3, 130.4, 124.5, 123.3, 120.9, 116.9, 113.2, 110.5, 57.0, 39.3; ESI-MS: m/z 354 [M+H]$^+$.

8-Bromo-4-chloro-2-(3,5-dimethyl-isoxazol-4-yl)-7-methoxy-quinoline

95%, $^1$HNMR (400 MHz, CDCl$_3$): δ=8.21 (d, J=9.2 Hz, 1H), 7.52 (s, 1H), 7.39 (d, J=9.6 Hz, 1H), 4.11 (s, 3H), 2.81 (s, 3H), 2.65 (s, 3H); $^{13}$CNMR (100 MHz, CDCl$_3$): δ=169.5, 158.9, 158.1, 152.1, 147.1, 143.1, 124.5, 120.7, 118.5, 115.4, 114.2, 110.9, 57.0, 13.4, 12.4; ESI-MS: m/z 369 [M+H]$^+$.

[4-(8-Bromo-4-chloro-7-methoxy-quinolin-2-yl)-thiazol-2-yl]-isopropyl-carbamic acid tert-butyl ester 85%, $^1$HNMR (400 MHz, CD$_2$Cl$_2$): δ=8.28 (s, 1H), 8.24 (d, J=9.2 Hz, 1H), 8.13 (s, 1H), 7.42 (d, J=9.2 Hz, 1H), 5.52 (m, 1H), 4.11 (s, 3H), 1.64 (s, 3H), 1.56 (m, 6H); ESI-MS: m/z 514 [M+H]$^+$

Step 4—Sulfonylation Reaction

The [4-(8-bromo-4-chloro-7-methoxy-quinolin-2-yl)-thiazol-2-yl]-isopropyl-carbamic acid tert-butyl ester obtained above is reacted with HCl and then with MeSO$_2$Na to provide 8-bromo-4-methanesulfonyl-2-(5-isopropylamino-thiazol-2-yl)-7-methoxy-quinoline in 85% yield.

Table of Suzuki coupling reagent and Product of Examples

| Entries | Boronic acids or esters | Product | Yields (%) |
|---|---|---|---|
| 1 | phenylboronic acid | 4-chloro-7-methoxy-8-bromo-2-phenylquinoline | 77 |
| 2 | 4-fluorophenylboronic acid | 4-chloro-7-methoxy-8-bromo-2-(4-fluorophenyl)quinoline | 80 |
| 3 | 4-ethoxyphenylboronic acid | 4-chloro-7-methoxy-8-bromo-2-(4-ethoxyphenyl)quinoline | 58 |

-continued

Table of Suzuki coupling reagent and Product of Examples

| Entries | Boronic acids or esters | Product | Yields (%) |
|---|---|---|---|
| 4 | 4-(trifluoromethyl)phenylboronic acid | 4-chloro-7-methoxy-8-bromo-2-[4-(trifluoromethyl)phenyl]quinoline | 60 |
| 5 | 3-methylphenylboronic acid | 4-chloro-7-methoxy-8-bromo-2-(3-methylphenyl)quinoline | 89 |
| 6 | 2-methoxyphenylboronic acid | 4-chloro-7-methoxy-8-bromo-2-(2-methoxyphenyl)quinoline | 64 |
| 7 | naphthalen-2-ylboronic acid | 4-chloro-7-methoxy-8-bromo-2-(naphthalen-2-yl)quinoline | 86 |
| 8 | furan-3-ylboronic acid | 4-chloro-7-methoxy-8-bromo-2-(furan-3-yl)quinoline | 94 |
| 9 | thiophen-3-ylboronic acid | 4-chloro-7-methoxy-8-bromo-2-(thiophen-3-yl)quinoline | 88 |
| 12 | 1H-indol-5-yl pinacol boronate | 4-chloro-7-methoxy-8-bromo-2-(1H-indol-5-yl)quinoline | 84 |

Table of Suzuki coupling reagent and Product of Examples

| Entries | Boronic acids or esters | Product | Yields (%) |
|---|---|---|---|
| 13 | | | 82 |
| 14 | | | 95 |
| 15 | | | 85 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

SPECIFIC EMBODIMENTS

A. A method for preparing a compound of formula (I), comprising reacting a 2,4-dichloro-7-alkoxy quinoline (III) with a brominating agent and then reacting the resulting 8-bromo-2,4-dichloro-7-alkoxy quinoline (IV) with a Suzuki coupling reagent selected from an R-boronic acid, R-boronate ester, R-potassium trifluoroborate or R-organoborane, by a Suzuki coupling reaction to replace the 2-chloro group with an R group according to the following reaction:

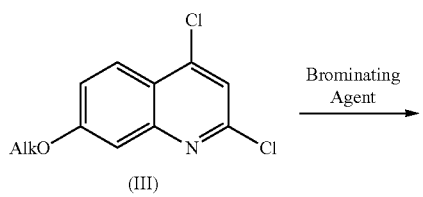

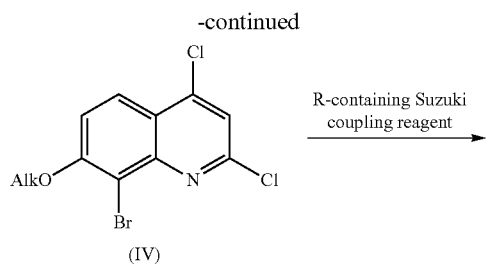

where R is: an aryl, heteroaryl, alkyl, alkenyl or alkynyl group, wherein the aryl and heteroaryl may each be optionally substituted with one or more groups independently selected from halogen, alkyl, halogenated alkyl, alkoxy, amido or amino optionally substituted by one or more alkyl and/or amino protecting groups; and Alk is a lower alkyl group.

B. The method of A. wherein R is phenyl, naphthyl, furanyl, thiophenyl, indolyl, pyrazolyl, isoxazolyl or thiazolyl, each optionally substituted one or more times by halogen, alkyl, alkoxy, halogenated alkyl, —NH-alkyl or —NP-alkyl, where P is an amino protecting group such as tert-butyl ester (Boc); and Alk is methyl.

C. The method of A. or B. further comprising preparing the 2,4-dichloro-7-alkoxy quinoline (III) by a cyclization reaction of an m-alkoxy aniline (II) with malonic acid in the presence of a chlorinating agent by the following reaction:

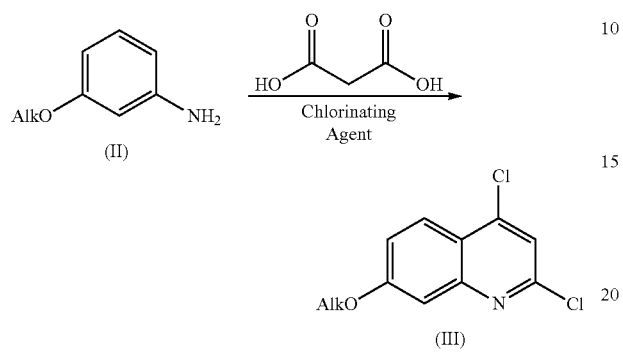

D. The method of C. wherein the chlorinating agent is phosphorus oxide trichloride (POCl$_3$), phosphorus pentachloride, thionyl chloride, or triphenylphosphine dichloride.

E. The method of A., B., C. or D., wherein the brominating agent is N-bromosuccinamide, bromine or 1,3-dibromo-5,5-dimethylhydantoin.

F. The method of A., B., C., D. or E., wherein the reaction with the brominating agent is conducted under acidic conditions and in the presence of an organic solvent which is immiscible in water.

G. The method F., wherein the acid is trifluoroacetic acid, sulfuric acid, benzensulfonic acid, or 10-camphorsulfonic acid and the solvent is methylene chloride H. The method of A., B., C., D., E., F. or G., wherein the Suzuki coupling reaction is conducted in the presence of a base and in the presence of a palladium catalyst I. The method of H., wherein the palladium catalyst is a palladium catalyst with phosphine ligands.

J. The method of H., wherein the palladium catalyst is Pd(PPh$_3$)$_4$.

K. The method of A., B., C., D., E., F., G., H., I., or J., wherein the Suzuki coupling reagent is an aryl boronic acid or ester and the 2-chloro group is replaced with the aryl group by the reaction.

L. The method of A., B., C., D., E., F., G., H., I., J. or K., wherein, the Suzuki coupling reaction is conducted with heating to 50-100° C. and under an inert atmosphere.

M. The method of A., B., C., D., E., F., G., H., I., J., K. or L., wherein the resulting compound (I) is further reacted to replace the 4-chloro group with —SO$_2$Me, as shown in Scheme II below:

Scheme II

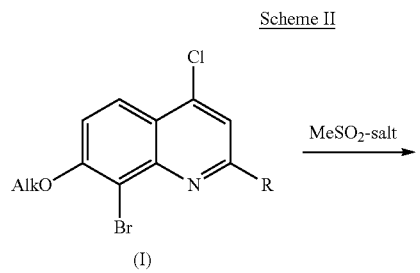

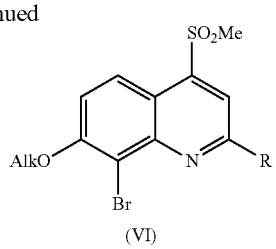

under acidic conditions.

N. A method for preparing a compound of formula (I), comprising reacting a 8-bromo-2,4-dichloro-7-alkoxy quinoline (IV) with a Suzuki coupling reagent selected from an R-boronic acid, R-boronate ester, R-potassium trifluoroborate or R-organoborane, by a Suzuki coupling reaction to replace the 2-chloro group with an R group according to the following reaction:

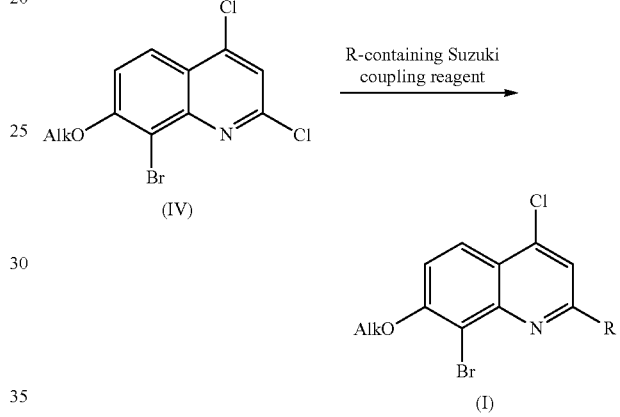

where R is: an aryl, heteroaryl, alkyl, alkenyl or alkynyl group, wherein the aryl and heteroaryl may each be optionally substituted with one or more groups independently selected from halogen, alkyl, halogenated alkyl, alkoxy, amido, or amino optionally substituted by one or more alkyl and/or amino protecting groups; and Alk is a lower alkyl group.

O. A method for preparing a compound of formula (IV), comprising reacting a 2,4-dichloro-7-alkoxy quinoline (III) with a brominating agent according to the following reaction:

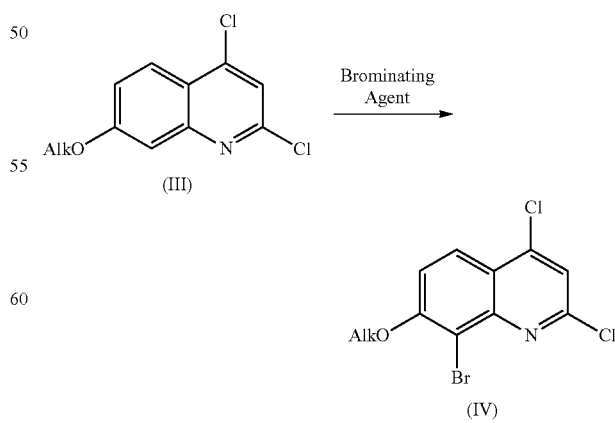

where Alk is a lower alkyl group.

P. A compound of formula (IV)

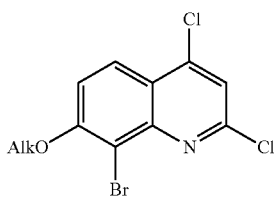

where Alk is a lower alkyl group.

Q. A compound of formula (V)

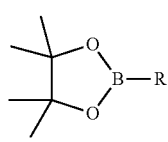

where R is thiazol-2-yl substituted in the 5-position by —NH-alkyl or —NP-alkyl, where P is an amino protecting group R. The compound of Q. where R is thiazol-2-yl substituted in the 5-position by —NP-isopropyl where P is a tert-butyl ester (Boc) amino protecting group.

We claim:

1. A method for preparing a compound of formula (I), comprising reacting a 2,4-dichloro-7-alkoxy quinoline (III) with a brominating agent and then reacting the resulting 8-bromo-2,4-dichloro-7-alkoxy quinoline (IV) with a Suzuki coupling reagent selected from an R-boronic acid, R-boronate ester, R-potassium trifluoroborate or R-organoborane, by a Suzuki coupling reaction to replace the 2-chloro group with an R group according to the following reaction:

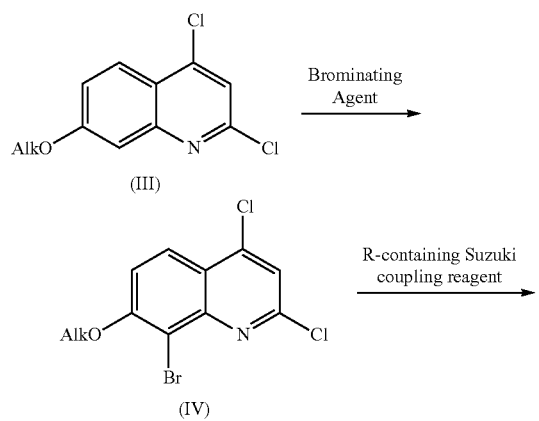

where R is: an aryl, heteroaryl, alkyl, alkenyl or alkynyl group, wherein the aryl and heteroaryl may each be optionally substituted with one or more groups independently selected from halogen, alkyl, halogenated alkyl, alkoxy, amido or amino optionally substituted by one or more alkyl and/or amino protecting groups; and Alk is a lower alkyl group.

2. The method according to claim 1 wherein R is phenyl, naphthyl, furanyl, thiophenyl, indolyl, pyrazolyl, isoxazolyl or thiazolyl, each optionally substituted one or more times by halogen, alkyl, alkoxy, halogenated alkyl, —NH-alkyl or —NP-alkyl, where P is an amino protecting group such as tert-butyl ester (Boc); and Alk is methyl.

3. The method according to claim 1, further comprising preparing the 2,4-dichloro-7-alkoxy quinoline (III) by a cyclization reaction of an m-alkoxy aniline (II) with malonic acid in the presence of a chlorinating agent by the following reaction:

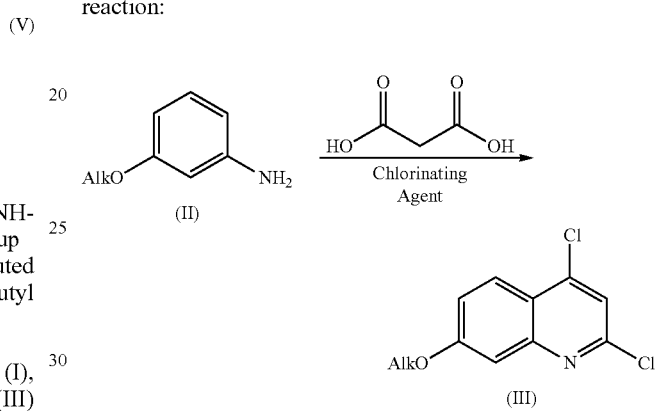

4. The method according to claim 1 wherein the brominating agent is N-bromosuccinamide, bromine or 1,3-dibromo-5,5-dimethylhydantoin.

5. The method according to claim 1 wherein the Suzuki coupling reaction is conducted in the presence of a base and in the presence of a palladium catalyst.

6. The method of claim 5 wherein the palladium catalyst is a palladium catalyst with phosphine ligands.

7. The method of claim 5 wherein the palladium catalyst is Pd(PPh$_3$)$_4$.

8. The method according to claim 1 wherein the Suzuki coupling reagent is an aryl boronic acid or ester and the 2-chloro group is replaced with the aryl group by the reaction.

9. The method of according to claim 1 wherein, the Suzuki coupling reaction is conducted with heating to 50-100° C. and under an inert atmosphere.

10. The method according to claim 1 wherein the resulting compound (I) is further reacted with an MeSO$_2$ salt to replace the 4-chloro group with —SO$_2$Me, as shown in Scheme II below:

Scheme II

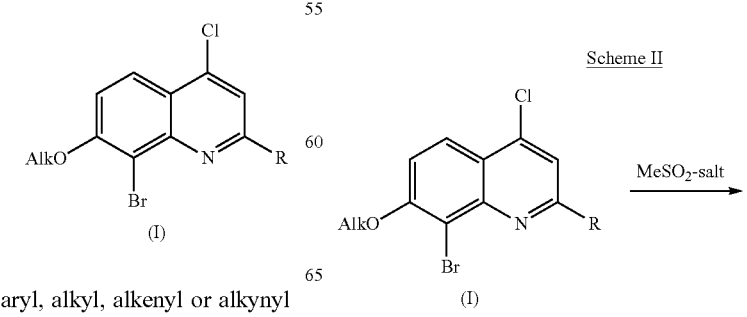

-continued

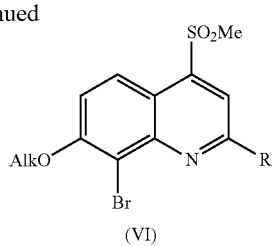

(VI)

under acidic conditions.

11. A method for preparing a compound of formula (I), comprising reacting a 8-bromo-2,4-dichloro-7-alkoxy quinoline (IV) with a Suzuki coupling reagent selected from an R-boronic acid, R-boronate ester, R-potassium trifluoroborate or R-organoborane, by a Suzuki coupling reaction to replace the 2-chloro group with an R group according to the following reaction:

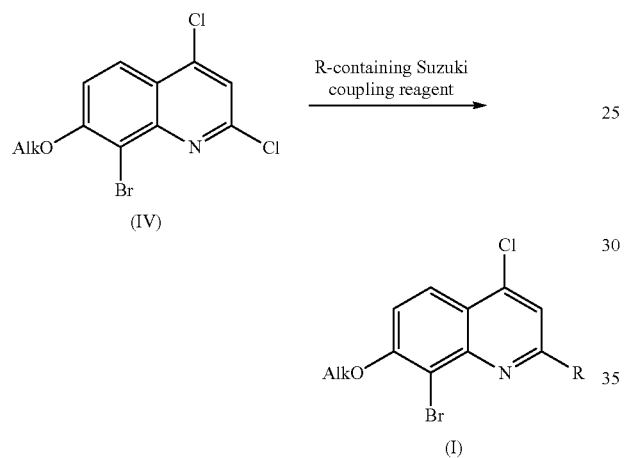

where R is: an aryl, heteroaryl, alkyl, alkenyl or alkynyl group, wherein the aryl and heteroaryl may each be optionally substituted with one or more groups independently selected from halogen, alkyl, halogenated alkyl, alkoxy, amido, or amino optionally substituted by one or more alkyl and/or amino protecting groups; and Alk is a lower alkyl group.

12. A method for preparing a compound of formula (IV), comprising reacting a 2,4-dichloro-7-alkoxy quinoline (III) with a brominating agent according to the following reaction:

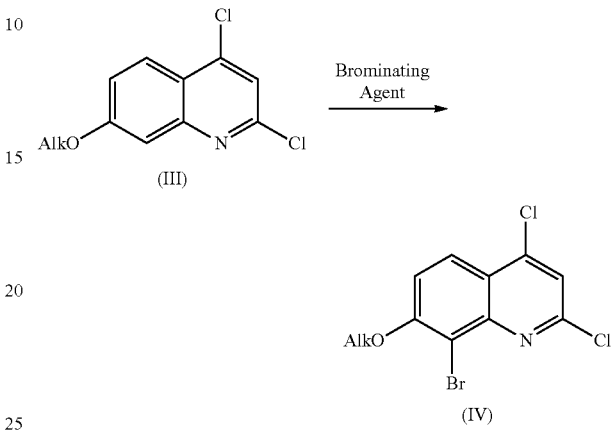

where Alk is a lower alkyl group.

13. A compound of formula (IV)

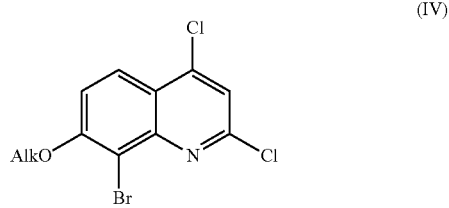

(IV)

where Alk is a lower alkyl group.

* * * * *